US006395788B1

(12) United States Patent
Iglehart, III

(10) Patent No.: US 6,395,788 B1
(45) Date of Patent: May 28, 2002

(54) METHODS AND COMPOSITIONS FOR TREATING OR PREVENTING SLEEP DISTURBANCES AND ASSOCIATED ILLNESSES USING VERY LOW DOSES OF CYCLOBENZAPRINE

(75) Inventor: Iredell W. Iglehart, III, Baltimore, MD (US)

(73) Assignee: Vela Pharmaceuticals, Inc., Lawrenceville, NJ (US)

( * ) Notice: Subject to any disclaimer, the term of this patent is extended or adjusted under 35 U.S.C. 154(b) by 0 days.

(21) Appl. No.: 09/637,557

(22) Filed: Aug. 11, 2000

Related U.S. Application Data

(60) Provisional application No. 60/148,881, filed on Aug. 13, 1999.

(51) Int. Cl.$^7$ ............................................. A61K 31/135

(52) U.S. Cl. ...................................................... 514/654
(58) Field of Search ................................ 514/656, 654, 514/239.2, 249, 220, 270, 253, 646, 649, 452

(56) References Cited

FOREIGN PATENT DOCUMENTS

| FR | 2100873 | 3/1972 |
| FR | 2121529 | 8/1972 |
| GB | 859187 | 1/1961 |

OTHER PUBLICATIONS

"Recognizing and treating fibromyalgia", Naurizio et al, 1997, The Nurse Practitioner, vol. 22, No. 12, p18(12).*
"The effects of bright light treatment on the symptoms of fibromyalgia", Reynolds et al., 1996, J. Rheumatol., 23(5): Abstract.*
D. Ang, et al., "Diagnosis, etiology, and therapy of fibromyalgia", *Comp. Ther.*, 25(4), pp. 221–227 (1999).
C.D. Barnes, et al., "Brainstem noradrenergic system depression by cyclobenzaprine," *Neuropharmacology*, 19, pp. 221–224 (1980).
J.V. Basmajian, "Cyclobenzaprine hydrochloride effect on skeletal muscle spasm in the lumbar region and neck: two double–blind controlled clinical and laboratory studies," *Arch. Phys. Med. Rehabil.*, 59, pp. 58–63 (1978).
R.M. Bennett, et al., "A comparison of cyclobenzaprine and placebo in the management of fibrositis," *Arthritis and Rheumatism*, 31(12), pp. 1535–1542 (1988).
D.G. Borenstein, et al., "Cyclobenzaprine and naproxen versus naproxen alone in the treatment of acute low back pain and muscle spasm," *Clinical Therapeutics*, 12(2), pp. 125–131 (1990).
S, Carette, et al., "Comparison of amitriptyline, cyclobenzaprine, and placebo in the treatment of fibromyalgia," *Arthritis & Rheumatism*, 37(1), pp. 32–40 (1994).

J.W. Commissiong, et al., "Cyclobenzaprine: a possible mechanism of action for its muscle relaxant effect," *Can. J. Physiol. Pharmacol.*, 59, pp. 37–44 (1981).
V. Fossaluzza, et al., "Combined therapy with cyclobenzaprine and ibuprofen in primary fibromyalgia syndrome," *Int. J. Clin. Pharm. Res.*, 12(2), pp. 99–102 (1992).
R.A. Gatter, "Pharmacotherapeutics in fibrositis," *The American Journal of Medicine*, 81(3A), pp. 63–66 (1986).
R.G. Godfrey, "A guide to the understanding and use of tricyclic antidepressants and in the overall management of fibromyalgia and other chronic pain syndromes," *Arch. Intern. Med.*, 156, pp. 1047–1052 (1996).
D.L. Goldenberg, "A review of the role of tricyclic medications in the treatment of fibromyalgia syndrome," *J. Rheumatol.*, 16(19), pp. 137–139 (1989).
D.L. Goldenberg, "Fibromyalgia syndrome a decade later," *Arch. Intern. Med.*, 159, pp. 777–785 (1999).
D.L. Goldenberg, "Treatment of fibromyalgia syndrome," *Rheumatic Disease Clinics of North America*, 15(1), pp. 61–71 (1989).
D. Hamathy, et al, "The plasma endorphin, prostaglandin and catecholamine profile of patients with fibrositis treated with cyclobenzaprine and placebo: a 5–month study," *Journal of Rheumatology*, 16(19), pp. 164–168 (1989).
W.A. Katz, et al., "Cyclobenzaprine in the treatment of acute muscle spasm: review of a decade of clinical experience," *Clinical Therapeutics*, 10(2), pp. 216–228 (1988).
C. Lines, et al., "Lack of sedative and cognitive effects of diphenhydramine and cyclobenzaprine in elderly volunteers," *Journal of Psychopharmacology*, 11(4), pp. 325–329 (1997).
D.R. Miller, et al., "Management of fibromyalgia, a distinct rheumatologic syndrome," *Clinical Pharmacy*, 6, pp. 778–786 (1987).
L.G. Quimby, et al., "A randomized trial of cyclobenzaprine for the treatment of fibromyalgia," *Journal of Rheumatology*, 16(19), pp. 140–143 (1989).
W.J. Reynolds, et al., "The effects of cyclobenzaprine on sleep physiology and symptoms in patients with fibromyalgia," *The Journal of Rheumatology*, 18(3), pp. 452–454 (1991).

(List continued on next page.)

Primary Examiner—Zorreh Fay
Assistant Examiner—Brian-Yong Kwon
(74) Attorney, Agent, or Firm—Fish & Neave; James F. Haley, Jr.; Kristin M. Joslyn

(57) ABSTRACT

The present invention relates to methods and compositions comprising a very low dose of cyclobenzaprine or metabolite thereof for preventing and treating sleep disturbances and illnesses manifested with sleep dysfunction including fibromyalgia syndrome, chronic fatigue syndrome, sleep disorders, psychogenic pain disorders or chronic pain syndromes or symptoms thereof. The present invention further relates to methods and compositions for treating sleep disturbances, chronic pain or fatigue in humans suffering from fibromyalgia syndrome, chronic fatigue syndrome, sleep disorders, psychogenic pain disorders, chronic pain syndromes using a very low dose of cyclobenzaprine.

29 Claims, No Drawings

OTHER PUBLICATIONS

T.J. Romano, "Fibromyalgia in children, diagnosis and treatment," *The West Virginia Medical Journal*, 87, pp. 112–114 (1991).

S. Santandrea, et al., "A double–blind crossover study of two cyclobenzaprine regimens in primary fibromyalgia syndrome," *The Journal of International Medical Research*, 21, pp. 74–80 (1993).

N.N. Share, "Cyclobenzaprine: studies on its site of muscle relaxant action in the cat," *Neuropharmacology*, 19, pp. 757–764 (1980).

H.A. Spiller, et al., "Five year multicenter retrospective review of cyclobenzaprine toxicity," *The Journal of Emergency Medicine*, 13(6), pp. 781–785 (1995).

F.J. Villani, et al., "Dialkylaminoalkyl Derivatives of 10, 11–Dihydro–5H–dibenzo[a,d]cycloheptene and related compounds," *J. Med. Pharm. Chem.*, 5, pp. 373–383 (1962).

F. Wolfe, et al., "The American College of Rheumatology 1990 criteria for the classification of fibromyalgia," *Arthritis and Rheumatism*, 33(2), pp. 160–172 (1990).

H.R. Khouzam, "Chronic Fatigue Syndrome: Update on Diagnosis and Treatment", *Consultant*, 40(8), pp. 1441–1450 (2000).

* cited by examiner

METHODS AND COMPOSITIONS FOR TREATING OR PREVENTING SLEEP DISTURBANCES AND ASSOCIATED ILLNESSES USING VERY LOW DOSES OF CYCLOBENZAPRINE

This application claims benefit of Prov. No. 60/148,881 filed Aug. 13, 1999.

TECHNICAL FIELD OF THE INVENTION

The invention relates to methods and compositions comprising very low doses of cyclobenzaprine. The methods and compositions are useful for treating or preventing sleep disturbances. Particularly, the methods and compositions of this invention are useful for treating patients suffering from fibromyalgia syndrome, prolonged fatigue, chronic fatigue, chronic fatigue syndrome, sleep disorders, psychogenic pain disorders, chronic pain syndromes, autoimmune diseases and symptoms thereof.

BACKGROUND OF THE INVENTION 1.1 Cyclobenzaprine

Cyclobenzaprine or 3-(5H-Dibenzo[a,d]cyclohepten-5-ylidene)-N,N-dimethyl-1-propanamine, is represented by the chemical formula:

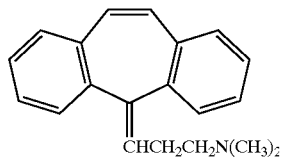

$CHCH_2CH_2N(CH_3)_2$

Cyclobenzaprine was first synthesized in 1961. [Villani, F. J., et al., "Dialkylaminoalkyl derivatives of 10,11-dihydro-511-dibenzo a,d cycloheptene and related compounds," *J. Med. Pharm. Chem.* 5:373–383 (1962)]. Cyclobenzaprine was approved by the U.S. Food and Drug Administration in 1977 for the treatment of acute muscle spasms of local origin. [Katz, W., et al., "Cyclobenzaprine in the Treatment of Acute Muscle Spasm: Review of a Decade of Clinical Experience," *Clinical Therapeutics* 10:216–228 (1988)]. Cyclobenzaprine is sold as a hydrochloride salt in a 10 mg non-scored tablet under the tradename Flexeril® (Merck and Co.) or as a generic (Genera, Warner-Chilcott, Duramed, Mylan, Endogenerics, and Watson) for use as a skeletal muscle relaxant. The pharmacokinetics of cyclobenzaprine metabolism have been well studied (e.g., Katz, et al., page 219, supra).

No indications of organ toxicity were found in cyclobenzaprine-treated patients at recommended doses. Toxic effects were reported, however, for three individuals who ingested between 260 to 900 mg of cyclobenzaprine. [Katz, et al.,"Cyclobenzaprine in the Treatment of Acute Muscle Spasm: Review of a Decade of Clinical Experience," *Clinical Therapeutics* 10:216–228 (1988)]

The principal side effects of cyclobenzaprine treatment are drowsiness, dry mouth or tongue, dizziness and bad taste. [Katz, W. A., et al.,supra.] Other less common side effects include nausea, tiredness, constipation, blurred vision, nervousness, confusion, abdominal pain and discomfort. Although cyclobenzaprine use has been reported to be associated with the side effects of drowsiness or tiredness, the utility of cyclobenzaprine as an agent for improving the quality of sleep, being a sleep deepener, or treating sleep disturbances when administered using a very low dosage regimen has not been recognized.

1.2 Sleep and Sleep Disturbance

Humans cycle repeatedly through four stages of sleep, each approximately 1½–2 hours long. Rapid eye movement (REM) sleep, associated with dreaming, occurs during Stage 1 sleep at the end of each cycle. Non-REM sleep occurs during Stage 3 and 4. When sleep quality is disturbed due to, for example, shallow sleep, frequent awakenings, or early awakenings, patients complain of "zombie", "zonked", "groggy", or "spacey" feelings, tiredness, feelings of being "run down," and having difficulty concentrating during waking hours. (The terms "zombie" and "spacey" are English slang words used to describe a state of mind wherein disconnected thoughts may be frequent and/or one may experience impaired short-term memory and/or concentration.)

1.3 Fibromyalgia Syndrome

Fibromyalgia syndrome (FMS), also known as fibrositis, is a chronic, non-inflammatory rheumatic disorder. The American College of Rheumatology (ACR) published a classification criteria for FMS in 1990. [Wolfe, F., et al., "The American College of Rheumatology 1990 criteria for the classification of Fibromyalgia: Report of the Multicenter Criteria Committee," *Arthritis and Rheumatism* 33:160–172 (1990)].

Some practitioners further classify fibromyalgia into two categories—primary or secondary-concomitant fibromyalgia. Generally, primary fibromyalgia syndrome can be considered fibromyalgia occurring in the absence of another significant condition whereas secondary-concomitant fibromyalgia can be considered fibromyalgia occurring in the presence of another significant rheumatic disorder, which may have been caused by or is merely associated with the patient's fibromyalgia. Secondary or concomitant fibromyalgia can include fibromyalgia in patients with classical or definite rheumatoid arthritis, osteoarthritis of the knee or hand, low back pain syndromes, cervical pain syndromes (or combinations thereof).

Studies exploring the relationship between sleep disturbances and fibromyalgia have been conducted. For example, Moldofsky et al. observed that seven fibromyalgia patients had alpha rhythm contamination in stage 4 sleep (non-REM sleep) and three fibromyalgia patients had an entire absence of delta waves (a hallmark of stage 4 sleep). [Moldofsky, H., et al., "Musculoskeletal symptoms and non-REM sleep disturbance in patients with 'fibrositis syndrome' and healthy subjects," *Psychosom. Med.* 37:341–51 (1975)] In another study, selected individuals who were not suffering from fibromyalgia prior to commencement of the study, were subjected to noise that artificially disrupted their slow-wave sleep. They experienced a similar alpha EEG sleep anomaly and complained of nonrefreshing sleep and diffuse myalgia/fatigue (Moldofsky, H. and P. Scarisbrick, "Induction of neurasthenic musculoskeletal pain syndrome by selective sleep stage deprivation," *Psychosom. Med.* 38:35–44 (1976)). The subjects did not show any increased muscle tenderness when deprived of REM sleep (Moldofsky, et al., 1976, supra).

Various drugs including analgesics, anti-inflammatory agents, psychotropic drugs, such as tricyclic antidepressants (TCAs), or high doses of cyclobenzaprine have been used with some success to treat some fibromyalgia patients.

TCAs have been typically administered in a dosage range of tens of milligrams/day with increasing dosages as needed. [Wysenbeek, J. et al. "Imipramine for the treatment of fibrositis: a therapeutic trial", *Ann. Rheum.* 44:752–753 (1985); Carette, S. et al. "Evaluation of amitriptyline in primary fibrositis", *Arthritis Rheum*, 29: 655–659 (1986);

Goldenberg, D. L., "A Review of the Role of Tricyclic Medications in the Treatment of Fibromyalgia Syndrome," *J. Rheumatology* 16:137–139, 139 (1989); Bryson, H. M. et al., "Amitriptyline: A Review of its Pharmacological Properties and Therapeutic Use in Chronic Pain States," *Drugs & Aging* 8:459–476, 461 (1996)].

Cyclobenzaprine has been administered to fibromyalgia patients typically in a dosage range of tens of milligrams per day. For example, several studies reported treatments of fibromyalgia or fibrositis using 10 to 40 mgs of cyclobenzaprine per day. [Bennett, R. et al. "A comparison of cyclobenzaprine and placebo in the management of fibrositis," *Arthritis Rheum.*, 31:1535–1542 (1988); Hamaty, Daniel et al., "The plasma endorphin, prostaglandin, and catecholamine profile of patients with fibrositis treated with cyclobenzaprine and placebo: a 5-month study," *J. Rheumatol.*, 16:140–143 (1989); Quimby, Lucy G. et al., "A randomized trial of cyclobenzaprine for the treatment of Fibromyalgia", *J. Rheumatol.*, 16:140–143 (1989)]

In another study, twelve fibromyalgia patients treated with twenty to forty mgs of cyclobenzaprine per day did not experience decreased pain, as monitored by tender point count and dolorimetry measurements. (Reynolds, W. J., et al., "The effects of cyclobenzaprine on sleep physiology and symptoms in patients with Fibromyalgia," *J. Rheumat.* 18:452–4 (1991)). Furthermore, the cyclobenzaprine did not favorably change the alpha non-REM EEG sleep anomaly (stage IV sleep) and mood ratings of the fibromyalgia patients. Thus, no specific effect of cyclobenzaprine in that dosage range on sleep physiology was documented.

Santandrea et al. compared two groups of fibromyalgia patients treated with either 10 mg/day or 30 mg/day of cyclobenzaprine. [Santandrea, S., et al., "A Double-Blind Crossover Study of Two Cyclobenzaprine Regimens in Primary Fibromyalgia Syndrome," *J. Int. Med. Res.* 21:74–80 (1993)] While both regimens resulted in a decline in the number of tender points and improvement in the quality of sleep, anxiety, fatigue, irritable bowel syndrome and stiffness of the patient, no significant difference in efficacy between the two therapeutic regimens was observed at any stage during the trial.

The only report of treatment with lower doses of cyclobenzaprine was anecdotal in its results. Miller et al. reported that some fibromyalgia patients responded "favorably" to treatment with five mgs per day of cyclobenzaprine, but did not indicate what the response was or its affect on sleep. [Miller, D. R. and R. D. Seifert, "Therapy Reviews: Management of Fibromyalgia, a Distinct Rheumatologic Syndrome," *Clinical Pharm.* 6:778–786, 785 (1987)].

Prior to this invention, the use of very low doses of cyclobenzaprine (i.e., a dosage regimen of less than 5 mg/day) to decrease sleep disturbances and alleviate the symptoms of fibromyalgia (e.g. pain, sleep disturbance) had not been reported.

1.4 Fatigue/Chronic Fatigue Syndrome

The United States Centers for Disease Control and Prevention characterize self-reported, persistent fatigue of 1 month or longer as prolonged fatigue. [http://www.cdc.gov/ncidod/diseases/cfs/defined3.htm; Jul. 16, 1999]. Chronic fatigue is defined as self-reported persistent or relapsing fatigue of 6 or more consecutive months (Id.).

Chronic fatigue syndrome ("CFS") is a clinically defined condition characterized by severe disabling fatigue and a combination of symptoms that prominently features self-reported impairments in concentration and short-term memory, sleep disturbances, and musculoskeletal pain. Chronic fatigue syndrome has also been referred to as "chronic fatigue and immune dysfunction syndrome" or "myalgic encephalitis".

Applicant believes that chronic fatigue syndrome and fibromyalgia are part of the same pathophysiological entity, wherein the dominant symptom of one subset of patients is fatigue, in others it is muscular pain, and in others it is both fatigue and muscular pain. There are certain symptoms (fever, swollen glands for example), however, which are found in a higher percentage of CFS patients than those with FMS. These symptoms, which manifest in a relatively small percentage of the total population of CFS patients, have been hypothesized to be attributable to a chronic infection by a viral agent, such as cytomegalovirus or Epstein Barr virus.

The use of very low dose cyclobenzaprine to treat prolonged fatigue, chronic fatigue or chronic fatigue syndrome has not been reported.

SUMMARY OF THE INVENTION

An object of this invention is to provide methods and compositions for treating a human suffering from sleep disturbances. Accordingly, the present invention relates to methods and compositions for treating or preventing sleep disturbances in humans using very low doses of cyclobenzaprine or metabolites thereof.

The methods and compositions of the invention are useful in treating sleep disturbances in general. Such sleep disturbances may be caused by stress or anxiety, disease, pain, the administration of a drug such as benzodiazepines, barbiturates, or alcohol. They are particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety.

In another embodiment, this invention provides methods and compositions for treating a human suffering from an illness caused by or exacerbated by sleep disturbances, and symptoms of such illness. Such illnesses include fibromyalgia, prolonged fatigue, chronic fatigue and chronic fatigue syndrome, sleep disorder, psychogenic pain disorder, and chronic pain syndrome. In the context of this embodiment of the invention, applicant has found that administration of less than 5 mg/day qHS of cyclobenzaprine is not only surprisingly effective at treating the sleep disturbance of many patients who suffer from fibromyalgia, and those other diseases, but the patients also experienced relief from fatigue and diffuse pain. Without wishing to be bound by theory, applicant believes cyclobenzaprine given at very low dose unexpectedly alleviates sleep disturbances and deepens sleep, which may be important for treating fibromyalgia and other illnesses associated with sleep disturbances.

Another object of this invention is to provide methods and compositions for treating sleep disturbances in a human who usually deepens sleep through exercise during waking hours but who cannot because of injury.

Another object of this invention is to provide improved methods and compositions for treating somatised symptoms, including pain, in patients suffering from irritable bowel syndrome and tension headaches, associated with fibromyalgia, chronic fatigue syndrome, psychogenic pain disorders, or chronic pain syndromes.

In still a further embodiment of this invention, the methods of this invention comprise the administration of very low doses of cyclobenzaprine or a metabolite thereof with one or more therapeutic agents such as a tricyclic antidepressant (TCA), a selective serotonin-reuptake inhibitor (SSRI); an atypical antidepressant; an anti-inflammatory agent; or an analgesic. In addition to working with these drugs to alleviate symptoms of underlying physiological problems, cyclobenzaprine also treats sleep disturbances caused by the administration of these drugs.

In another embodiment, the methods of this invention further comprise the administration of very low doses of cyclobenzaprine or a metabolite thereof in combination with psychotherapy or light-box therapy.

Another object of this invention is to provide a composition comprising a very low dose of cyclobenzaprine or a metabolite thereof as a single unit or composition that is pre-prepared into separable portions that comprise a very low dose of cyclobenzaprine or metabolite thereof, which composition is better for treating patients and aiding practitioners to determine appropriate dosage regimens for patients. Such compositions, as well as the other compositions of this invention, may additionally comprise one or more therapeutic agents such as a TCA, a SSRI, an atypical antidepressant, an anti-inflammatory or an analgesic.

These and the other objects of this invention are accomplished by methods and compositions characterized by very low dosage regimens of cyclobenzaprine. Such methods and compositions unexpectedly treat or prevent sleep disturbances.

DETAILED DESCRIPTION OF THE INVENTION

In these applications the following terms are used:

"Chronic fatigue": a persistent or relapsing fatigue of 6 or more consecutive months. In a preferred embodiment, the symptom to be treated is fatigue.

"Chronic fatigue syndrome" or "CFS": a chronic, remitting, debilitating disorder, which predominantly features self-reported impairments in concentration and short-term memory, and disturbances in sleep and emotions. CFS patients as defined herein should have self-reported persistent or relapsing fatigue of 6 or more consecutive months. Symptoms of chronic fatigue syndrome are known in the art. In a preferred embodiment, the symptom to be treated is fatigue.

"Chronic pain syndrome" or "CPS": two types of chronic pain: (i) chronic pain arising from identifiable, ongoing illnesses (e.g., injury, cancer, arthritis), wherein the cause of the pain is evident or (ii) chronic pain which is a psychologic-physiologic disability arising from an unidentifiable or a seemingly unexplainable source. The term chronic pain syndrome is most often used in conjunction with the latter type of CPS (type II above). The latter type CPS, which does not necessarily respond to traditional pain remedies such a narcotics, has been referred to as a learned response syndrome which seems to involve a self-perpetuating alteration in pain perception and an amplified response to the perceived pain. CPSs according to this invention include chronic fatigue syndrome (CFS), myalgia encephalitis, fibrositis, and fibromyalgia syndrome. Symptoms of chronic pain syndrome are known in the art.

"Cyclobenzaprine or metabolite thereof": includes cyclobenzaprine or a metabolite thereof or prodrugs of cyclobenzaprine or a metabolite thereof, in the form of a pharmaceutically acceptable salt, hydrate, or solvate thereof.

"Fibromyalgia" (or "fibromyalgia syndrome"): a chronic, non-inflammatory rheumatic disorder traditionally characterized by stiffness or diffuse pain, aches, muscle soreness, sleep disturbances or fatigue. The pain is generally widespread and generally localized at specific "tender points," which ay bring on widespread pain and muscle spasm when touched. Other symptoms include mental and emotional disturbances such as poor concentration and irritability, neuropsychiatric symptoms such as depression and anxiety, joint swelling, headache, numbness.

"Prolonged fatigue": a persistent fatigue of 1 month or longer. In a preferred embodiment, the symptom to be treated is fatigue.

"Psychogenic pain disorder": a pain syndrome exacerbated or caused predominantly by psychological factors, in accordance with the Diagnostic and Statistical Manual of Mental Disorders (DSM-IV) [American Psychiatric Association: Diagnostic and Statistical Manual of Mental Disorders, Fourth Edition. Washington, D.C., American Psychiatric Association, 1994]. According to the DSM-IV, pain associated with a general medical condition alone, absent psychological contributing factors, is a purely physical syndrome that should not be characterized as a mental disorder. Accordingly, the term "psychogenic pain disorder" is used herein to denote pain with a clinically significant psychological aspect. Acute psychogenic pain disorder is characterized by pain lasting less than 6 months, while chronic psychogenic pain disorder is characterized by pain longer than 6 months in duration. The essential feature of psychogenic pain disorder is pain that is the predominant focus of the clinical presentation and is of sufficient severity to warrant clinical attention. The pain causes significant distress or impairment in social, occupational, or other important areas of function. Symptoms of psychogenic pain disorders are known in the art.

"Sleep disorder": any one of four major categories of sleep dysfunction. (DSM-IV, pp. 551–607; See also *The International Classification of Sleep Disorders: (ICSD) Diagnostic and Coding Manual,* 1990, American Sleep Disorders Association.) One category, primary sleep disorders, comprises sleep disorders that do not result from another mental disorder, a substance, or a general medical condition. They include without limitation primary insomnia, primary hypersomnia, narcolepsy, circadian rhythm sleep disorder, nightmare disorder, sleep terror disorder, sleepwalking disorder, REM sleep behavior disorder, sleep paralysis, day/night reversal and other related disorders; substance-induced sleep disorders; and sleep disorders due to a general medical condition. A second category comprises those sleep disorders attributable to substances, including medications and drugs of abuse. A third category comprises sleep disturbances arising from the effects of a general medical condition on the sleep/wake system. A fourth category of sleep disorders comprises those resulting from an identifiable mental disorder such as a mood or anxiety disorder. Symptoms of each category of sleep disorder are known in the art.

"Sleep disturbance": an impairment in refreshing sleep. Such a clinical diagnosis may be made based on a patient's self described feeling of fatigue upon waking or the patient's report of poor quality sleep. Such impediments to good quality sleep may be described as shallow sleep or frequent awakenings which may be associated with alpha rhythm contamination in stage 4 sleep (non-REM sleep) or absence of delta waves during deeper physically restorative sleep. Such "sleep disturbances" do not rise to the level of a "sleep disorder" as defined in the DSM-IV, although they may share one or more symptom in common. Symptoms of sleep disturbances are known in the art. Among them are "zombie", "zonked", "groggy", or "spacey" feelings, tiredness, feelings of being "run down," and having difficultly concentrating during waking hours.

"Somatization": an unconscious process whereby psychological distress or anxiety is expressed as a physical symptom.

"Very low dose" or "very low dosage regimen": the administration of less than 5 mg/day of cyclobenzaprine or metabolite thereof.

Cyclobenzaprine: A compound having the chemical formula:

CHCH₂CH₂N(CH₃)₂

Metabolites of cyclobenzaprine useful according to the methods of this invention are metabolites that have substantially the same activity or better as cyclobenzaprine in alleviating sleep disturbances or one of more of the symptoms of his/her illness. Cyclobenzaprine metabolites that may be useful according to this invention include CBP 10,11-trans-dihydriol, N-desmethyl-2-hydroxycyclobenzaprine, 3-hydroxycyclobenzaprine, N-desmechylcyclobezaprine cyclobenzaprine N-oxide or a chiral isomer of these metabolites.

"Cyclobenzaprine" as used in describing the invention also includes prodrugs, i.e. drugs that are metabolized in vivo into the active agent. Prodrugs useful according to this invention are those that have substantially the same activity or better than cyclobenzaprine in alleviating sleep disturbance or one of more of the symptoms of his/her illness. Methods for making such prodrugs are readily know in the art (e.g., Balant, L. P., "Prodrugs for the Improvement of Drug Absorption Via Different Routes of Administration," *Eur. J. Drug Metab. Pharmacokinet.* 15:143–153 (1990); and Bundgaard, H., "Novel Chemical Approaches in Prodrug Design," *Drugs of the Future* 16:443–458 (1991); incorporated by reference herein).

Pharmaceutically salts of cyclobenzaprine useful according to the methods of this invention are salts prepared from pharmaceutically acceptable non-toxic acids including inorganic acids and organic acids. In one preferred embodiment, the salt is a hydrochloride salt.

A composition according the present invention comprises less than 5 mg of cyclobenzaprine or a metabolite thereof as a single unit (hereinafter, "composition"), or as a unit that is pre-prepared into separable portions (hereinafter, "separable composition"), each portion of which comprises a very low dose of cyclobenzaprine or metabolite thereof. In one embodiment, the composition or each portion of the separable composition comprises less than or equal to 2.5 mgs of cyclobenzaprine or metabolite thereof. In another embodiment, the composition or each portion of the separable composition comprises less than or equal to 1 mg of cyclobenzaprine or metabolite thereof. For example, a separable composition is a scored tablet.

A composition according the present invention may also comprise less than 5 mg of cyclobenzaprine or a metabolite thereof given with other therapeutic agents according to this invention, including a TCA, an SSRI, an atypical antidepressant, an anti-inflammatory, or an analgesic. Thus, the composition or separable composition according to this invention can comprise one or more TCA, SSRI, atypical antidepressant, SNRI, anti-inflammatory, and/or analgesics.

An atypical antidepressant according to this invention are antidepressants which are not TCAs or SSRIs, e.g., serotonin agonist and reuptake inhibitors (SARIs) such as nefazodone (Serzone™) or trazodone (Desyrel™); Norepinephrine-Dopamine Reuptake Inhibitors (NDRIs) such as bupropion (Wellbutrin™); and norepinephrine reuptake inhibitors (NRIs) such as reboxetine (Edronax™) and serotonin-norepinephrine reuptake inhibitors (SNRIs) such as venlafaxine (Effexor™), amoxapine and maprotiline. In a preferred embodiment, the therapeutic agent is a TCA and/or SSRI.

In one embodiment, the TCA is administered in a dose less than 25 mg/day. A TCA according to this invention may be selected from the group consisting of imipramine, trimipramine, nortriptyline, amitriptyline, doxepin, protriptyline, clomipramine, or desipramine. In a preferred embodiment, the TCA is nefazodone (Serzone™).

In another embodiment, the SSRI is administered in a dosage of 40 or less mg per day. An SSRI according to this invention may be selected from the group consisting of fluoxetine (Prozac™), fluvoxamine maleate (Luvox™), paroxetine (Paxil™, Seroxar™, or Aropax™), sertraline (Zoloft™), and citalopram (Celexa™). In a preferred embodiment, the SSRI is sertraline (Zoloft™).

Said therapeutic agent according to the methods of this invention may be administered before, during or after the administration of cyclobenzaprine.

The methods and compositions of this invention are useful for treating or preventing a sleep disturbance.

In a preferred embodiment, the sleep disturbance is associated with the group consisting of fibromyalgia syndrome, prolonged fatigue, chronic fatigue, chronic fatigue syndrome, a sleep disorder, a psychogenic pain disorder, and chronic pain syndrome (type II).

In a more preferred embodiment, the symptoms to be treated are selected from the group consisting of "zombie", "zonked", "groggy", or "spacey" feelings, tiredness, feelings of being "run down," and having difficultly concentrating during waking hours.

According to the methods of this invention, one or more of the above-identified symptoms are alleviated in fibromyalgia patients. In one preferred embodiment, the symptom of pain is alleviated.

The methods and compositions of this invention are useful for treating sleep disturbances in primary and secondary-concomitant fibromyalgia syndrome.

The methods and compositions of this invention are also useful for treating people that have sleep disturbance caused by the administration of drugs that cause sleep disturbances, such as benzodiazepines, barbiturates and alcohol. Benzodiazepines include chlordiazepoxide, clorazepate, diazepam, flurazepam, halazepam, prazepam, alprazolam, chlonazepam, flunitrazepam, lorazepam, midazolam, oxazepam, quazepam, temazepam, and troazolam. Barbiturates include phenobarbital, amobarbital, probarbital, butabarbital, mephobarbital, pentobarbital, secobarbital, and talbutal.

The methods and compositions of this invention are also useful for treating a human suffering from an autoimmune disease, or a human suffering from or expected to suffer from stress or anxiety.

According to the methods of this invention, very low dose cyclobenzaprine or metabolites thereof, may be administered sequentially or concurrently with other standard treatments for sleep disturbance, fatigue, stress, anxiety, fibromyalgia, prolonged pain, chronic pain, chronic fatigue syndrome, sleep disorders, psychogenic pain disorders, or chronic pain syndromes.

The period of treatment should be carried out for as long as necessary to alleviate one or more of the symptoms of the illness being treated, either in a single, uninterrupted session of visits or in discrete sessions. In a preferred embodiment, if a sleep disturbance is being treated, the treatments will preferably be carried out such that the patient achieves deep, refreshing sleep. Deep, refreshing sleep is not be confused with sleep which is merely longer in duration. Alternatively, treatments may be carried out until the patient feels an increased energy or a greater sense of well being. Generally, cyclobenzaprine therapy can be carried out indefinitely to alleviate the symptoms of interest and frequency of dosage may be changed to be taken as needed.

Any suitable route of administration may be employed for providing the patient with an effective dosage of cyclobenzaprine. For example, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques.

Dosage forms include tablets, scored tablets, coated tablets, caplets, capsules (e.g. hard gelatin capsules), troches, dragees, dispersions, suspensions, solutions, patches and the like, including sustained release formulations well known in the art. In one preferred embodiment, the dosage form is a scored tablet.

The compositions and separable compositions useful according to this invention include those suitable for oral, rectal, transdermal, sublingual, and parenteral administration (including subcutaneous, intramuscular, intrathecal and intravenous), although the most suitable route in any given case will depend on the nature and/or severity of the condition being treated. A preferred route of administration according to the methods of the present invention is the oral route. The composition may be conveniently presented in unit dosage form and prepared by any of the methods well-known in the art of pharmacy.

The compositions or separable compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The compositions according to this invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

Compositions or separable compositions of this invention may also be administered in the form of suppositories for rectal administration. These compositions or separable compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A typical oral formulation for coated tablets would consist of the following:

| Formula | Quantity per Tablet (mg.) |
|---|---|
| cyclobenzaprine | 1.0 |
| Lactose | 74.0 |
| Corn Starch | 35.0 |
| Water (per thousand Tablets) | 30.0 ml* |
| Magnesium Stearate | 1.0 |
| Corn Starch | 25.0 |

*The water evaporates during manufacture.

The active ingredient (cyclobenzaprine) is blended with the lactose until a uniform blend is formed. The smaller quantity of corn starch is blended with a suitable quantity of water to form a corn starch paste. This is then mixed with said uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

Tablets are coated by standard aqueous or nonaqueous techniques. For example, 2.5 mg of hydroxypropylmethylcellulose can be dissolved in 25 mg of deionized water. An aqueous (10 mg) suspension of 1.88 mg talc, 0.5 mg of titanium dioxide, 0.1 mg of yellow iron oxide, and 0.02 mg of red iron oxide is stirred into this solution. The coating suspension is sprayed on the tablets and the coated tablets are dried overnight at 45° C.

Quantification of improvement may be measured according to methods known in the art. For example, pain may be measured using tender point count, the McGill Pain Questionnaire, the Arthritis Impact Measurement Scales (AIMS), the Sickness Impact Profile (SIP), the Health Assessment Questionnaire (HAQ) functional disability index, the Symptom Checklist-90R, and dolorimeter scores. A practitioner may reliably assess changes in condition by comparing treatment results over a time span. (Alarcon, Graciela, et al., "Advances in the Treatment of Fibromyalgia: Current Status and Future Directions", *Am. J. Med. Sciences,* 315:397–404 (1998).)

The quality of sleep ("sleep disturbance") may be determined, inter alia, by asking the patient if he/she awakened tired or nonrefreshed "never," "seldom," "often or usually," or "always." Replies of "often or usually" or "always" may be scored as positive and other replies as negative. Patients reports of well-being or relief from "zombie" or "spacey" feelings, feelings of being "run down," and having difficultly concentrating during waking hours are indications of better quality of sleep or deep, refreshing sleep.

The magnitude of a prophylactic or therapeutic dose of the active ingredient (i.e., cyclobenzaprine or metabolite thereof) in the prevention or treatment of a human will vary with the type of affliction, the severity of the patient's affliction and the route of administration. The dose and dose frequency will also vary according to the age, weight and response of the individual patient. However, the dosage will not equal or exceed 5 mgs per day. In a preferred embodiment, one dose is given at bed time or up to several hours before bedtime to facilitate the achievement of deep, refreshing sleep. Bedtime may be any hour of the day at which a person engages in the most extensive period of sleep.

The treating physician will know how to increase, decrease or interrupt treatment based upon patient response. Generally, however, treatment or prevention of an illness treated according to the methods of this invention will be timed to coincide with exposure to biochemical, environmental, or hormonal stimuli likely to trigger sleep disturbance, illnesses treatable according to this invention or symptoms thereof.

The various terms described above such as "therapeutically effective amount," are encompassed by the above-described dosage amounts and dose frequency schedule.

Throughout this specification and claims, the word "comprise," or variations such as "comprises" or "comprising," will be understood to imply the inclusion of a stated integer or group of integers but not the exclusion of any other integer or group of integers.

In order that this invention be more fully understood, the following examples are set forth. These examples are for the purpose of illustration only and are not to be construed as limiting the scope of the invention in any way.

EXAMPLES

Example 3

A.S., a 27 year old female homemaker, had been diagnosed with fibromyalgia ten years previously, but had done well on no medication until exacerbation of disease activity post-partem two years prior to presentation. Symptoms then subsided until the 26th week of her second pregnancy, when she was seen in rheumatologic consultation complaining of multiple areas of soreness and fatigue, associated with disrupted sleep. On examination she had a total of 16 tender points, with unremarkable bloodwork including thyroid functions and ESR. After delivery, with continued symptoms (the patient was not breast feeding), she was begun on cyclobenzaprine ½ of a 10 mg tablet qHS, but she telephoned to state that she felt "like a zombie." On a dosage of ¼ tablet (2.5 mg) qHS she subsequently found progressive improvement. She reported complete abatement of multiple areas of soreness, aches and pains and disrupted sleep.

Example 4

G.R., a 49 year old female executive, presented with fatigue and poor sleep and diffuse pain, and on examination had tenderness over bilateral trochanters, bilateral medial knees, and paralumbar areas. Bloodwork was unremarkable, and her previous imipramine 10 mg p.o. qHS was changed to cyclobenzaprine, 10 mg p.o. qHS, but the dose had to be reduced to ½ tablet (5 mg) due to mental cloudiness. After her symptoms abated, she discontinued treatment. However, six years later her symptoms recurred, with similar findings in the office, but this time ½ tablet (5 mg) left her "groggy" in the morning. She was on a dose of ⅓ tablet of cyclobenzaprine (3.33 mg). The treatment alleviated her symptoms with no adverse effects. She achieved complete resolution of her tender points and reported that she experienced improved energy and deep sleep.

Example 5

M.W., an 80 year old widow, complained of occasional periods of poor sleep with frequent awakening and resultant exhaustion. The patient was prescribed cyclobenzaprine 10 mg p.o. qHS, which helped her sleep but caused "grogginess" during the day as did ½ tablet (5 mg). The patient's dosage regimen was switched to ¼ tablet (2.5 mg) per day qHS. The patient reported that the new dosage regimen helped her to sleep deeply, allowing her to awaken refreshed without any adverse mental effect.

Example 6

C.S., a 35 year old female homemaker, presented with complaints of chest pain previously attributed to her known history of mitral valve prolapse. She also complained of a several year history of fatigue. On physical exam she exhibited focal tenderness of the parasternal area (reproducing her chest pain), as well as her paracervical, bilateral medial epichondyles medial knees, and paralumbar areas. Her exam was otherwise normal except for a midsystolic click. Comprehensive bloodwork, including thyroid function testing and erythrocyte sedimentation rate (ESR), was unremarkable. The diagnosis of fibromyalgia was made, and she was begun on cyclobenzaprine, 10 mg p.o. qHS, but on telephone followup she complained of feeling "groggy," and therefore her dose was decreased to ¼ to ½ tablet (approximately 2.5–5 mg). She felt markedly improved on this dose, with a feeling of deeper sleep, and with resolution of both her chest pain and other sore areas, and of her fatigue.

Example 7

M.T., a 68 year old active grandmother, presented with the new onset of cervical and lumbar muscular pains associated with poor quality sleep and fatigue. The patient was diagnosed with fibromyalgia. Physical therapy did not help significantly, and although she was averse to medication, agreed to a trial of cyclobenzaprine, 10 mg p.o. qHS. In telephone followup she found this dose to be helping her muscular pains. She experienced dry mouth and constipation. On 5 mg, the side effects continued and wanted to discontinue the medication entirely. However, on ¼ pill (2.5 mg), she found this dose to be very effective for both her muscular pains and her sleep disturbance and fatigue with no side effects.

Example 8

H.P., a 41 year old female homemaker, presented with complaints of diffuse pain and fatigue. Examination revealed multiple tender points in the parasternal and paralumbar areas, as well as tenderness of medial knees, without evidence of synovitis. Comprehensive bloodwork, including thyroid function testing and ESR, was unremarkable. She was diagnosed with fibromyalgia and was begun on cyclobenzaprine, 10 mg p.o. qHS, but complained of increased A.M. fatigue and constipation; however, she subsequently did well when prescribed ¼ to ½ (2.5–5 mg) tablet. She demonstrated improved sleep, decreased muscular pain, and improved sense of well-being.

Example 9

C.M., a 43 year old female homemaker, presented with complaints of right trapezius spasm. She had recently been started on paroxetine, 20 mg p.o. qd for mild depression, and had also noted disrupted sleep quality with frequent awakening with resultant fatigue and daytime somnolence. Her pains subsequently generalized to involve multiple areas of soft tissue pain, and on examination she had sixteen tender points that were exquisitely sensitive to moderate pressure. Comprehensive bloodwork, including thyroid function testing, was unremarkable. She was diagnosed with fibromyalgia and was begun on cyclobenzaprine 10 mg p.o. qHS for the diagnosis of fibromyalgia and possible sleep disturbance due to the SSRI paroxetine. In followup she complained of feeling "zonked" in the morning on 10 mg. Subsequently she did well when she was prescribed ¼ to ½ (2.5–5 mg) cyclobenzaprine qHS.

Example 10

M.P., a 29 year old female homemaker, had recently given birth to a healthy baby, and in during the later stages of pregnancy and in the post-partem period noted fatigue and exhaustion associated with multiple areas of muscular soreness. On examination she exhibited tenderness over both medial epichondyles and her right trapezius muscle. (She was examined on a "good day," and by history had multiple other similarly tender areas.) She was diagnosed with fibromyalgia and was begun on cyclobenzaprine, 10 mg p.o. qHS but noted prompt increase in her A.M. fatigue. On ½ tablet (5 mg), she continued to feel "zonked out." Subsequently on ¼ tablet (2.5 mg), she did not experience side effects however at this dose it did not help her pains. She subsequently did well on a trial of nortriptyline.

Example 11

K.L., a 48 year old female executive, presented with complaints of "burning pains" in her muscles, associated with sleep disturbance with frequent awakening and resultant fatigue. Her symptoms had begun soon after she had been treated with sertraline for mild depression. Examination showed multiple tender points, absence of synovitis, and comprehensive bloodwork including thyroid functions and ESA was unremarkable. She was diagnosed with fibromyalgia and was begun on cyclobenzaprine 10 mg p.o. qHS, but complained of feeling "groggy" in the A.M. When prescribed ¼ to ½ tablet (2.5–5 mg), she noted significant improvement in her sleep and muscle pain, with an increase in her energy level.

Example 12

J.T., a 50 year old executive, had been tried on multiple medications by a "fibromyalgia specialist," who according to the patient had performed over $2,000 in blood tests, diagnosing "yeast infection in the blood" and multiple allergies. The patient indeed did have fibromyalgia with multiple tender points and unremarkable bloodwork. She was treated with ¼ to ½ tablet (2.5–5 mg) of cyclobenzaprine and telephoned soon thereafter to report "the cloud has lifted;" she felt markedly improved with deeper sleep, improved energy and decreased fatigue, and decrease in muscle pain.

Example 13

J.H., a 53 year old female school teacher, presented with longstanding fatigue and muscle soreness. On examination, she had 16 tender points and unremarkable comprehensive bloodwork, including thyroid function testing and ESR. She was diagnosed with fibromyalgia and was treated with cyclobenzaprine 10 mg p.o. qHS, but found she was too "spacey" to function teaching in the morning, and had the same experience taking ½ tablet (5 mg). Despite weighing 232 lbs, a dosage of ¼ tablet (2.5 mg) deepened her sleep and eliminated all of her soreness. She shortly thereafter stopped her cyclobenzaprine in order to be more arousable should her ill mother call for her in the middle of the night; this led to an immediate return of all of her previous symptoms.

Example 14

A.G., a 46 year old female homemaker, complained of disrupted sleep with frequent awakening attributed to temporary domestic stress. She was treated with cyclobenzaprine 10 mg p.o. qHS, but found she was too "spacey" in the morning; a dosage of ¼ tablet (2.5 mg) allowed her to sleep soundly without affecting her mental status.

Example 15

D.B., a 55 year old male aerospace engineer, presented with exhaustion and fatigue, concerned he was suffering from chronic Lyme disease. Upon further questioning, he had been sleeping poorly for many months, with frequent awakening and daytime somnolence, nearly falling asleep at the wheel. His wife reported no loud snoring or periods of apnea. Physical examination was unremarkable, as was comprehensive bloodwork, including Lyme serologies, thyroid function testing, and ESR. A trial of cyclobenzaprine 10 mg helped deepen his sleep, but made him feel too "groggy" during the day; however, ¼ to ½ tablet (2.5–5 mg) led to improved sleep and increased energy, with resolution of his daytime somnolence.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all documents contained herein are hereby incorporated by reference.

I claim:

1. A method for treating a sleep disturbance comprising the step of administering to a human in need of treatment for such sleep disturbance a composition comprising cyclobenzaprine or a metabolite, prodrug, or salt thereof in an amount of less than 5 mg/day, wherein the human is not suffering from the fibromyalgia syndrome.

2. The method according to claim 1, wherein the sleep disturbance is associated with an illness selected from the group consisting of, prolonged fatigue, chronic fatigue, chronic fatigue syndrome, a sleep disorder, a psychogenic pain disorder, and chronic pain syndrome (type II).

3. The method according to claim 1, wherein such sleep disturbance is associated with the administration of a drug selected from the group consisting of a benzodiazepine, a barbiturate, and alcohol.

4. The method according to claim 3 wherein the drug is a benzodiazepine.

5. The method according to claim 4 wherein the benzodiazepine is selected from the group consisting of chlordiazepoxide, clorazepate, diazepam, flurazepam, halazepam, prazepam, alprazolam, clonazepam, flunitrazepam, lorazepam, midazolam, oxazepam, quazepam, temazepam, and triazolam.

6. The method according to claim 3 wherein the drug causing sleep disturbance is a barbiturate.

7. The method according to claim 6 wherein the barbiturate is selected from the group consisting of phenobarbital, amobarbital, aprobarbital, butabarbital, mephobarbital, pentobarbital, secobarbital, and talbutal.

8. The method according to claim 3 wherein the drug is alcohol.

9. The method according to claim 1, wherein the human is suffering from an autoimmune disease.

10. The method according to claim 1, wherein the human is suffering from or is expecting to suffer stress or anxiety.

11. A method for treating or preventing a sleep disorder comprising the step of administering to a human in need of treatment for a sleep disorder cyclobenzaprine or a metabolite thereof in an amount of less than 5 mg/day, wherein the human is not suffering from fibromyalgia syndrome.

12. The method according to claim 1 or 11, wherein cyclobenzaprine or metabolite thereof is administered in an amount of 2.5 mg or less per day.

13. The method according to claim 1 or 11, wherein cyclobenzaprine or metabolite thereof is administered in an amount of 1.0 mg or less per day.

14. The method according to claim 1 or 11, wherein cyclobenzaprine or metabolite thereof is administered in one dose before bedtime.

15. The method according to claim 1 or 11, wherein cyclobenzaprine or metabolite thereof is administered in combination with psychotherapy.

16. The method according to claim 1 or 11, wherein cyclobenzaprine or metabolite thereof is administered in combination with light-box therapy.

17. The method according to claim 1 or 11, wherein cyclobenzaprine or metabolite thereof is administered in combination with other drug therapies for treatment of the sleep disturbance or its symptoms or the sleep disorder or its symptoms.

18. The method according to claim 1 or 11, wherein cyclobenzaprine is administered as a hydrochloride salt.

19. The method according to claim 1 or 11, further comprising the step of administering a therapeutic agent sequentially or concurrently with said cyclobenzaprine or metabolite thereof.

20. The method according to claim wherein the therapeutic agent is selected from the group consisting of a TCA, an SSRI, an atypical antidepressant, an SNRI, an NRIS, an anti-inflammatory, and an analgesic.

21. The method according to claim 20, wherein the TCA is selected from the group consisting of imipramine, trimipramine, nortriptyline, amitriptyline, doxepin, protriptyline, clomipramine and desipramine.

22. The method according to claim 20, wherein the SSRI is selected from the group consisting of fluoxetine, fluvoxamine maleate, paroxetine, sertraline, and citalopram.

23. The method according to claim 20, wherein the atypical antidepressant is selected from the group consisting of serotonin agonist and reuptake inhibitors (SARIs); Norepinephrine-Dopamine Reuptake Inhibitors (NDRIs); norepinephrine reuptake inhibitors (NRIs) and serotonin-norepinephrine reuptake inhibitors (SNRIs).

24. The method according to claim 1 or 11, wherein the cyclobenzaprine or metabolite thereof is administered orally or parentally.

25. The method according to claim 1 or 11, wherein the cyclobenzaprine or pharmaceutically acceptable salt thereof is administered as a tablet or a capsule.

26. The method according to claim 23, wherein the atypical antidepressant is nefazodone (Serzone™) or trazodone (Desyrel™).

27. The method according to claim 23, wherein the atypical antidepressant is bupropion (Wellbutrin™).

28. The method according to claim 23, wherein the atypical antidepressant is reboxetine (Edronax™).

29. The method according to claim 23, wherein the atypical antidepressant is venlafaxine (Effexor™), amoxapine or maprotiline.

* * * * *